United States Patent [19]

McWhorter

[11] 4,015,605
[45] Apr. 5, 1977

[54] DRAINAGE RECEPTACLE

[75] Inventor: Daniel M. McWhorter, Arlington Heights, Ill.

[73] Assignee: The Kendall Company, Boston, Mass.

[22] Filed: Oct. 28, 1975

[21] Appl. No.: 626,428

[52] U.S. Cl. .............................. 128/294; 128/275; 128/2 F
[51] Int. Cl.$^2$ ......................................... A61F 5/42
[58] Field of Search ............... 128/275.1, 276, 277, 128/278, 2 F, DIG. 24, DIG. 5, 275, 274, 283, 284, 294, 295; 73/422

[56] References Cited

UNITED STATES PATENTS

| | | | |
|---|---|---|---|
| 3,343,542 | 9/1967 | Ericson | 128/275 |
| 3,774,591 | 11/1973 | Corbin et al. | 128/2 F |

Primary Examiner—Robert W. Michell
Assistant Examiner—Henry S. Layton
Attorney, Agent, or Firm—Powell L. Sprunger

[57] ABSTRACT

A drainage receptacle comprising, a collection bag having a back wall and a front wall at least partially defining a chamber in the bag, with the front wall being movable toward and away from the back wall and having an opening communicating with the chamber. The receptacle has a connector attached to the front wall and having a cavity communicating with the chamber through the opening. The receptacle also has a drainage conduit communicating with the connector cavity through an inlet port spaced from the chamber for passage of liquid from the conduit through the opening into the chamber and collection therein. The receptacle also has a sampler conduit communicating with the connector cavity through an outlet port, in order that the connector may be pressed toward the back wall to impede passage of liquid from the drainage conduit into the chamber until the liquid passes through the sampler conduit for obtaining a sample.

18 Claims, 6 Drawing Figures

U.S. Patent      April 5, 1977      4,015,605
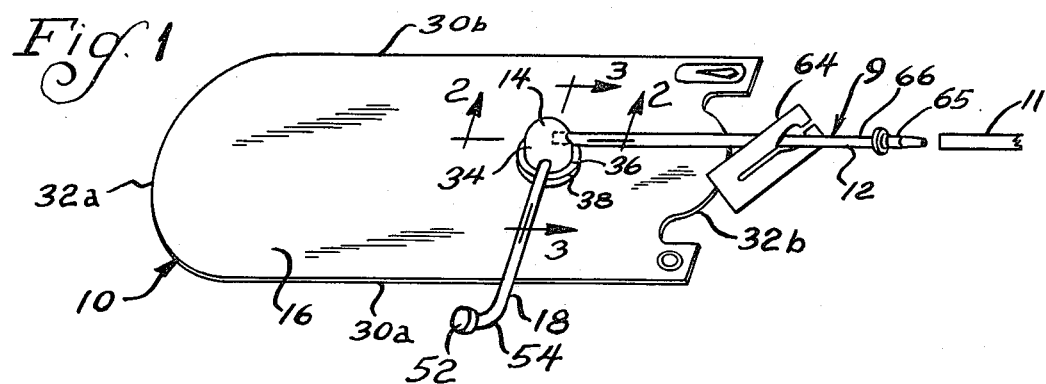
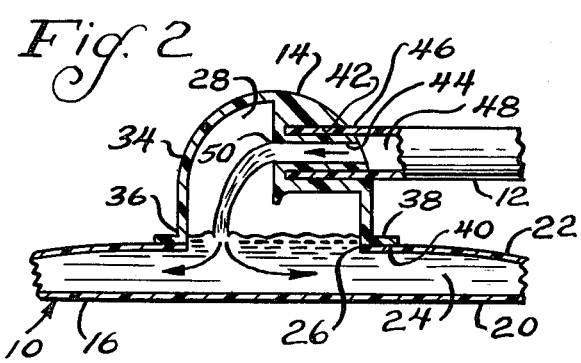
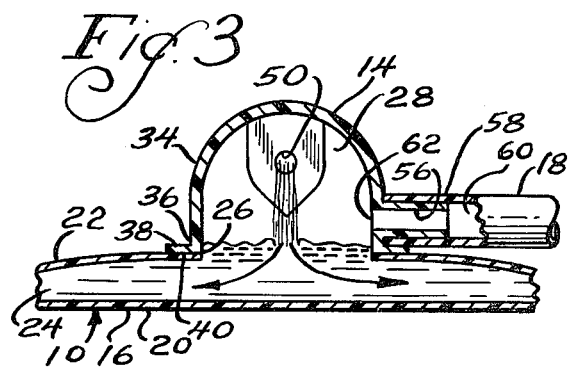
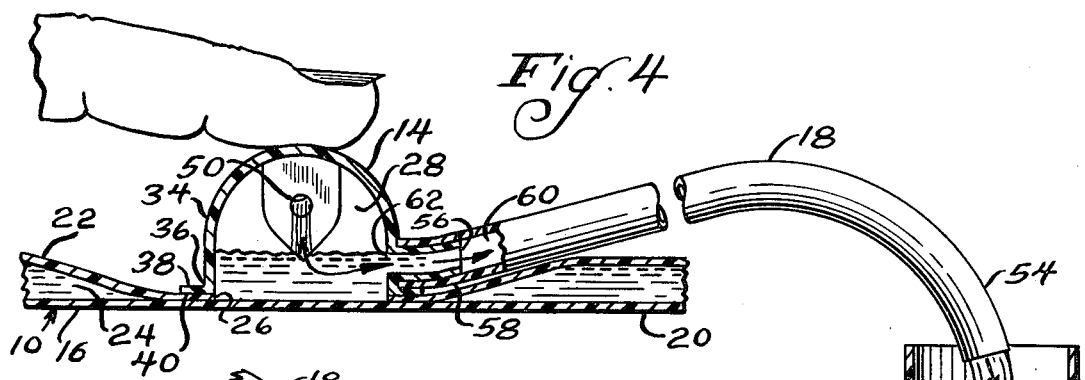
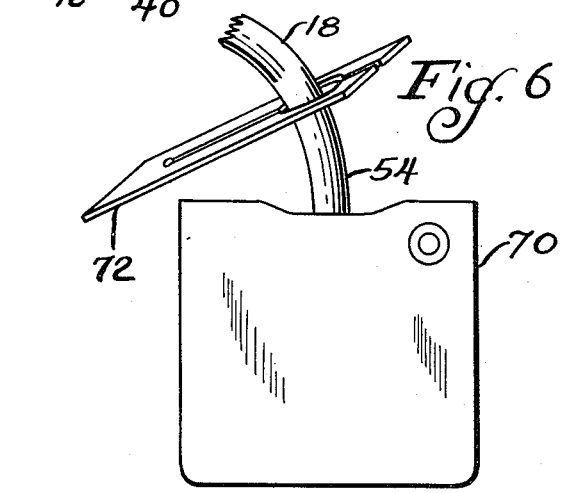
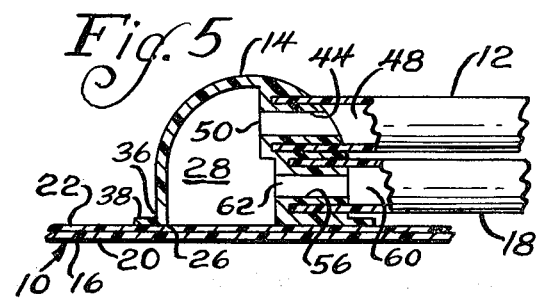

DRAINAGE RECEPTACLE

BACKGROUND OF THE INVENTION

The present invention relates to liquid drainage systems, and more particularly to drainage receptacles for such systems.

In the past, urine has been drained from a patient's bladder during catheterization in the following manner. A distal end of a catheter is positioned in the bladder, with a proximal end of the catheter located outside the patient's body, and the proximal end of the catheter is attached to a drainage bag or to a drainage tube which communicates with the drainage bag. Urine drains from the bladder through the catheter to a chamber in the bag where it is collected.

Since the use of the drainage system poses the danger of introducing infection into the body cavity, it is necessary to maintain the system in a sterile condition. In the past, difficulties have been encountered in obtaining a sample of urine from the systems without contaminating the sample and system. For example, if the catheter is removed from the drainage tube to obtain the sample, bacteria may be introduced into the system during this procedure. Moreover, the procedure of disconnecting and again connecting the catheter has been found inconvenient to hospital personnel.

SUMMARY OF THE INVENTION

A principal feature of the invention is the provision of a drainage receptacle for a liquid drainage system which permits a liquid sample to be obtained in a simplified and aseptic manner.

In a preferred form, the receptacle of the present invention comprises, a collection bag having a flexible back wall for placement on a generally horizontal supporting surface, a flexible front wall having an opening extending through the front wall, and a collection chamber. The receptacle also has a connector attached to the front wall around the opening, and having a planar base facing toward the back wall and a cavity communicating with the chamber through the opening. The receptacle has a drainage conduit communicating with the connector cavity through an inlet port spaced from the opening. The receptacle also has a sampler conduit communicating with the connector cavity through an outlet port.

A feature of the present invention is that liquid normally drains in the system from the drainage conduit through the inlet port, the connector cavity, and the opening into the bag chamber for collection therein.

Another feature of the invention is that the base is normally spaced from the back wall during liquid drainage to permit unimpeded flow of liquid from the connector cavity into the bag chamber.

Yet another feature of the invention is that the base may be moved toward the back wall of the bag to impede passage of liquid from the connector cavity into the bag chamber.

Still another feature of the invention is that the connector base may be pressed sufficiently hard against the back wall of the bag to prevent passage of liquid from the drainage conduit into the bag chamber.

A feature of the invention is that in this configuration the liquid passing from the drainage conduit collects in the connector cavity and then passes through the outlet port into the sampler conduit.

Thus, a feature of the invention is that a sample of the liquid may be obtained from the sampler conduit.

Another feature of the invention is that the sample is obtained in a simplified and aseptic manner without the necessity of removing a catheter from the drainage conduit.

Yet another feature in an embodiment of the invention is the provision of a sampler bag attached to an outer end of the sampler conduit for collecting the sample.

Further features will become more fully apparent in the following description of the embodiments of this invention and from the appended claims.

DESCRIPTION OF THE DRAWINGS

In the drawings:

FIG. 1 is a perspective view of a liquid drainage system and receptacle of the present invention;

FIG. 2 is a fragmentary sectional view taken substantially as indicated along the line 2—2 of FIG. 1;

FIG. 3 is a fragmentary sectional view taken substantially as indicated along the line 3—3 of FIG. 1;

FIG. 4 is a fragmentary elevational view, taken partly in section, showing the receptacle while taking a liquid sample;

FIG. 5 is a fragmentary sectional view of another embodiment of the receptacle of the present invention; and FIG. 6 is a fragmentary elevational view of a sampler bag of the present invention.

DESCRIPTION OF THE PREFERRED EMBODIMENTS

Referring now to FIG. 1, there is shown a liquid drainage system 9 having a drainage receptacle generally designated 10 and a catheter 11. The drainage receptacle 10 has a liquid drainage tube or conduit 12, a connector 14, a drainage bag or container 16, and a sampler tube or conduit 18.

Referring to FIGS. 1-3, the collection or drainage bag 16 has a flexible or rigid back wall 20 and a flexible front wall 22 defining a collection chamber 24 intermediate the back and front walls 20 and 22. The front wall 22 has an opening 26 communicating between a cavity 28 in the connector 14 and the chamber 24. As shown in FIG. 1, the bag 16 has a pair of side edges 30a and 30b, and a pair of end edges 32a and 32b connecting the side edges 30a and 30b. In a convenient form, the front and back walls 22 and 20, respectively, may be made of a fluid impervious thermoplastic material, and may be sealed, such as by heating, along the side edges 30a and b and end edges 32a and b to form the collection bag 16.

With reference to FIGS. 1-3, the connector 14 may be molded from a thermoplastic material by injection molding, and in the embodiment shown comprises a drip chamber having a generally dome shape. The connector 14 has an outer side wall 34 partially defining the cavity 28, and a base 36 comprising an outwardly directed flange 38 extending peripherally around a lower portion of the connector 14 and defining a generally planar surface 40 facing toward the back wall 20 of the collection bag 16. The flange 38 may be attached to the outer surface of the front wall 22 around the opening 26 by suitable means, such as sealing, as shown in FIGS. 2 and 3, although the connector may include a base located inside the front wall, if desired.

As illustrated in FIG. 2, the connector 14 has an annular recess 42 defining a tubular extension or nipple 44 which is received in proximal end 46 of the drainage conduit 12 which in one form may be a catheter for insertion into the patient's body, if desired. The proximal end 46 of the drainage conduit 12 is snugly received in the recess 42 of the connector to secure the drainage conduit 12 to the connector 14. In this configuration, a lumen 48 in the drainage conduit 12 communicates through the tubular extension 44 and an inlet aperture or port 50 to the cavity 28 of the connector 14. Although the connector 14 may define the inlet port 50, it will be apparent that the drainage conduit 12 may extend into the connector cavity 28, such that the proximal end 46 of the drainage conduit defines the inlet port 50. As shown, the inlet port 50 of the connector 14 is spaced from the chamber 24 of the collection bag 16, and when the back wall 20 of the bag 16 is placed on a generally horizontal supporting surface, the inlet port 50 is located at a level above the opening 26 of the collection bag 16.

As illustrated in FIG. 1, the sampler conduit 18 has a cap 52 releasably attached to an outer end 54 of the sampler conduit 18 remote the connector 14 to close the outer end 54 of the conduit 18. As shown in FIG. 3, the connector 14 has a tubular extension of nipple 56 received in an inner end 58 of the sampler conduit 18 to secure the sampler conduit 18 to the connector 14. A lumen 60 in the sampler conduit 18 communicates through the tubular extension 56 and an outlet aperture or port 62 to the cavity 28 of the connector 14. Although in a preferred form the connector 14 defines the outlet port 62, it will be apparent that the connector and sampler conduit 18 may be secured together with the sampler conduit extending into the connector cavity 28, such that the inner end 58 of the sampler conduit 18 defines the outlet port 62. As shown, the outlet port 62 is spaced from the bag chamber 24, and in a preferred form is located at a level intermediate the level of the inlet port 50 and the opening 26 of the collection bag 16 or the base of the connector. In one embodiment, the distance between the outlet port 62 and the bag opening 26 may be approximately one-half the distance between the bag opening 26 and the inlet port 50. However, as will be seen below, the outlet port 62 may be located at the same level as the inlet port 50 or above the level of the inlet port 50.

With reference to FIGS. 1–3, it will be seen that in the particular embodiment shown, the portions of the drainage conduit 12 and sampler conduit 18 adjacent the connector 14 are disposed generally at a right angle relative each other, such that the inlet and outlet ports 50 and 62 are generally disposed 90 degrees peripherally around the connector 14. However, it will be understood that the sampler conduit 18 may be disposed at any suitable location peripherally around the connector 14, such as the configuration illustrated in FIG. 5. In this embodiment, the sampler conduit 18 is generally aligned with the drainage conduit 12 adjacent the connector, such that the outlet port 62 is located below the inlet port 50 and simplifying the manufacturing procedure in molding the connector 14.

Referring again to FIG. 1, in the illustrated embodiment the sampler conduit 18 extends from the connector 14 past the side edge 30a of the collection bag 16, while the drainage conduit 12 extends from the connector 14 in a direction generally parallel to the side edge 30a of the bag 16. A clamp 64 may also be positioned on the drainage conduit 12 to selectively open or close this conduit.

With reference to FIGS. 1–3, during catheterization a distal end of the catheter 11 is positioned in the bladder of a patient with a proximal end of the catheter extending outside the patient's body and being attached to a connector 65 at a distal end 66 of the drainage conduit. During normal drainage of the system 9, the front wall 22 of the bag 16 moves away from the back wall 20 which is supported on a generally horizontal surface, such that the base 36 of the connector 14 is spaced from the bag back wall 20. Thus, urine drains from the patient's bladder through the catheter 11, the drainage tube 12, the inlet port 50, the connector cavity 28, and the bag opening 26 into the bag chamber 24 for collection therein.

When it is desired to obtain a urine sample, the cap 52 may be removed from the sampler conduit 18, and, as shown in FIG. 4, the connector 14 may be pushed toward the back wall 20 of the collection bag 16, such that the base flange 38 and base surface 40 causes sealing engagement of the bag front wall 22 against the back wall 20. In this configuration, the connector base 36 prevents passage of urine from the connector cavity 28 into the bag chamber 24. Thus, the incoming urine passing through inlet port 50 collects in the connector cavity 28, as shown, until it passes through the outlet port 62 and the sampler conduit 18 into a suitable container C for collection. During the sampling procedure, the level of urine in the connector cavity 28 of the preferred embodiment does not rise to the level of the inlet port 50, since the urine passes out through the outlet port 62 which is at a lower level than the inlet port 50. However, if desired, the outlet port 62 may be located at the same level as the inlet port 50 or above the inlet port 50, since the pressure developed by the patient's bladder is sufficient to prevent backflow of urine into the drainage conduit 12.

When a sufficient amount of urine has been collected in the container C, the connector 14 may be released by the user's finger to permit the connector base 36 and bag front wall 22 to move away from the back wall 20 of the bag 16 and again permit normal liquid drainage into the bag chamber 24. Also, the cap 52 may be replaced on the outer end 54 of the sampler conduit 18 to close the sampler conduit. Thus, in this manner, an uncontaminated sample of urine may be readily obtained from the system without contaminating the system and sample. Although the connector base or bag front wall may be sealingly engaged against the bag back wall during sampling, the connector may be depressed only sufficiently to impede passage of liquid from the connector cavity 28 into the bag chamber 24.

As shown in FIG. 6, the outer end 54 of the sampler conduit 18 may be received in a sample bag 70 which is attached by suitable means to the sampler conduit 18. Accordingly, the urine sample may be collected in the bag 70, and when a sufficient amount of urine has been obtained the conduit 18 may be severed above a clamp 72. The severed conduit portion connected to the bag 70 may be closed by the clamp 72 to provide a self-contained container for retaining the sample. Also, the severed end of the sampler conduit remaining attached to the drainage receptacle may be closed by a cap of the type previously described.

The foregoing detailed description is given for clearness of understanding only, and no unnecessary limitations should be understood therefrom, as modifications will be obvious to those skilled in the art. For example, although the bag 16 has been described previously for use in a horizontal configuration, it will be apparent that the bag may be supported in an upright position, such that the connector may be pressed toward the generally vertically disposed back wall to obtain a sample through the sampler conduit. The connector may be located adjacent a side edge of the bag, and the connector and back wall may be squeezed together between the user's fingers.

I claim:

1. A drainage receptacle, comprising:
   a collection bag having a lower back wall for placement on a generally horizontal supporting surface, an upper flexible front wall having an opening extending through the front wall, and a collection chamber intermediate said front and back walls;
   a connector having a base attached to said front wall around the periphery of said opening, said base having a generally planar surface defining a lowermost portion of said connector and facing toward said back wall, said connector having a cavity located only above said front wall and communicating with said chamber through said opening;
   a drainage conduit communicating with the connector cavity through an inlet port spaced above said front wall opening, whereby liquid normally drains from said conduit through said opening into the chamber while the connector base is spaced from the back wall of said bag; and
   a sampler conduit communicating with the connector cavity through an outlet port located at a level intermediate the inlet port and said front wall opening, whereby the base of said connector may be moved toward the back wall of the bag to prevent passage of liquid from the drainage conduit into the chamber until liquid passes into the sampler conduit for obtaining a sample.

2. The receptacle of claim 1 wherein said connector comprises a drip chamber.

3. The receptacle of claim 1 wherein said connector generally has the shape of a dome.

4. The receptacle of claim 1 wherein said bag has at least one side edge, said connector is spaced from said side edge, and said sampler conduit extends from said connector toward said side edge.

5. The receptacle of claim 4 wherein said sampler conduit extends past said side edge.

6. The receptacle of claim 4 wherein said drainage conduit extends from said connector in a direction generally parallel with said side edge adjacent the connector.

7. The receptacle of claim 1 wherein said drainage conduit and sampler conduit extend from said connector generally at right angles relative each other adjacent the connector.

8. The receptacle of claim 1 wherein said drainage conduit and sampler conduit are generally aligned with each other adjacent said connector.

9. The receptacle of claim 1 including a closure cap removably secured to an outer end of said sampler conduit remote said connector.

10. The receptacle of claim 1 including a sample container attached to an outer end of the sampler conduit remote said connector.

11. The receptacle of claim 1 wherein said connector includes a tubular extension attached to said drainage conduit, with said tubular extension defining said inlet port.

12. The receptacle of claim 1 wherein said connector includes a tubular extension attached to said sampler conduit, with said tubular extension defining said outlet port.

13. The receptacle of claim 1 wherein said inlet port and outlet port are disposed at approximately 90° peripherally around the connector.

14. The receptacle of claim 1 wherein said outlet port is located at a level spaced a distance from said opening approximately one-half the distance between said opening and the level of the inlet port.

15. The receptacle of claim 1 wherein said base comprises an outwardly directed flange extending peripherally around the connector.

16. The receptacle of claim 15 wherein said flange is attached to the front wall of said bag around said opening.

17. The receptacle of claim 16 wherein an inner surface of said flange is attached to an outer surface of said front wall.

18. The receptacle of claim 1 wherein the drainage conduit comprises a urinary catheter.

* * * * *